United States Patent [19]
Silverstein et al.

[11] Patent Number: 5,888,724
[45] Date of Patent: Mar. 30, 1999

[54] DETECTION OF HIGH ONCOGENIC-RISK PAPILLOMA VIRUS IN HIGH GRADE CERVICAL LESIONS AND CANCERS BY A PCR/ELISA ASSAY

[75] Inventors: Saul J. Silverstein, Irvington; Octavian Lungu, New York; Thomas C. Wright, Irvington; Ralph M. Richart, Oakdale, all of N.Y.

[73] Assignee: The Trustees of Columbia University in the City of New York, New York, N.Y.

[21] Appl. No.: 479,777

[22] Filed: Jun. 7, 1995

Related U.S. Application Data

[63] Continuation of Ser. No. 390,684, Feb. 17, 1995, abandoned.
[51] Int. Cl.$^6$ .............................. C12Q 1/70; C12Q 1/68; C12P 19/34
[52] U.S. Cl. ................................. 435/5; 435/91.2; 435/6
[58] Field of Search .................................. 435/5, 6, 91.1, 435/91.2

[56] References Cited

U.S. PATENT DOCUMENTS

| | | | |
|---|---|---|---|
| 5,501,947 | 3/1996 | Emery et al. | 435/5 |
| 5,580,970 | 12/1996 | Hendricks et al. | 536/24.32 |

OTHER PUBLICATIONS

Brown et al. (1994) Clin. Diag. Virol. 2:41–51.
Reischl et al. (1994) Mol. Biotechnol. 1 : 229–40.
Kohsaka et al. (1993) Nucl. Acids Res. 21 : 3469–72.
Haras et al. (1994) CAH. SANTE 4 : 43–52.
Zachar et al. (1991) J. Virol. Methods 33:391–5.
Hataya et al. J. Virol. Methods 46:223–26.
He et al. (1993) J. Clin. Microbiol. 31:1040–7.
Hermans (1990) J. Clin Microbiol.28:1204–13.
Coutlee et al. (1995) J. Clin. Microbiol. 33:1973–8.
Begum et al. (1993) J. Clin. Microbiol. 31:3153–6.
Alard et al. (1993) BioTechniques 15:730–2.
Beaucage and Carruthers (1981) *Tetrahedron Lett.* 22:1859–1862.
Donnan, S.P.B., et al. (1989) "Reproductive and Sexual Risk Factors and HPV Infection in Cervical Cancer Among Hong Kong Chinese" *Int. J. Epidemiol.* 18:32–6.
Lungu, O., et al. (1992) "Relationship of HPV Type to Grade of Cervical Intraepithelial Neoplasia" *JAMA* 267:2493–6.
Lungu, O., et al. (1995) "A Polymerase Chain Reaction–Enzyme–Linked Immunosorbent Assay Method for Detecting Human Papillomavirus in Cervical Carcinomas and High––Grade Cervical Cancer Precursors" *Obstet. Gynecol.* 85:337–342.
Maxam, A.M., and Gilbert, W. (1980) *Methods in Enzymology* Grossman, L., and Moldave, D., eds. Academic Press, New York 65:499–560.
Munoz, N., et al. (1992) "The Casual Link Between HPV and Invasive Cervical Cancer: A Population–Based Case–Control Study in Colombia and Spain" *Int. J. Cancer* 52:743–9.
Needham–VanDevanter, D.R., et al. (1984) *Nucleic Acids Res.* 12:6159–6168.
Pearson, J.D. and Regnier, F.E. (1983) *J. Chrom.* 255:137–149.
Schmauz, R., et al. (1989) "Multiple Infections in Cases of Cervical Cancer From a High–Incidence Area in Tropical Africa" *Int. J. Cancer* 43:805–9.
Wright, T.C., and Richart, R.M. (1990) "Role of HPV in Pathogenesis of Genital Tract Warts and Cancer" *Gynecol. Oncol.* 37: 151–64.
Bauer, H. M., et al. (1991) "Genital human papillomavirus infection in female university students as determined by a PCR–based method" *JAMA* 265:472–477.
Gissman, L. and Schneider, A. (1986) "Human papillomavirus DNA in preneoplastic and neoplastic genital lesions" *Viral Etiology of Cancer* (Peto,RR.,zurHausen, H. 217–224) Cold Spring Harbor, N.Y.: Cold Spring Harbor Laboratory.
Kirnbauer, R., et al. (1994) "A virus–like particle enzyme–linked immunosorbent assay detects serum antibodies in a majority of women infected with human papillomavirus type 16" *J. Natl. Cancer Inst.* 86:494–499.
Lorincz, A.T., et al. (1987) "Oncogenic association of specific human papillomavirus types with cervical neoplasia" *J. Natl. Cancer Inst.* 79:671–677.
Lorincz, A.T., et al. (1992) "Human papillomavirus infection of the cervix: Relative risk association of 15 common anogenital types" *Obstet. Gynecol.* 79:328–337.
Lungu, O., et al. (1991) "Biologic properties and nucleotide sequence analysis of human papillomavirus type 51" *J. Virol.* 65:4216–4225.

(List continued on next page.)

*Primary Examiner*—Lisa B. Arthur
*Attorney, Agent, or Firm*—John P. White; Cooper & Dunham LLP

[57] ABSTRACT

This invention provides a method of detecting a high oncogenic-risk type human papillomavirus in a subject which comprises: obtaining from a subject a specimen containing cervical cells and treating the specimen so as to recover nucleic acid molecules present in the cervical cells; contacting the resulting nucleic acid molecules with multiple pairs of single-stranded labeled oligonucleotide primers capable of specifically hybridizing with a different high oncogenic-risk type of human papillomavirus; amplifying any nucleic acid molecules to which a pair of primers hybridizes so as to obtain a double-stranded amplification product and treating any double-stranded amplification product so as to obtain single-stranded nucleic acid molecules; contacting any resulting single-stranded nucleic acid molecules with multiple single-stranded labeled oligonucleotide probes which are capable of specifically hybridizing with such high oncogenic-risk types of human papillomavirus; contacting any resulting hybrids with a marked antibody capable of specifically forming a complex with the labeled probe, when the probe is present in such a complex; and detecting the presence of any resulting complexes, the presence thereof being indicative of the presence of a high oncogenic-risk type human papillomavirus in the initial specimen.

9 Claims, 3 Drawing Sheets

OTHER PUBLICATIONS

Lungu, O., et al. (1992) "Typing of human papillomaviruses by polymerase chain reaction amplification with L1 consensus primers and RFLP analysis" *Mol. Cell Probes* 6:145–152.

Onda. T., et al. (1993) "Association of the antibodies against human papillomavirus 16 E4 and E7 proteins with cervical cancer positive for human papillomavirus DNA" *Int. J. Cancer* 54:624–628.

Peng, H., et al. (1991) "Human papillomavirus types 16 and 33, herpes simplex virus type 2 and other risk factors for cervical cancer in Sichuan province, China" *Int. J. Cancer* 47:711–716.

Reid, R., et al. (1987) "Sexually transmitted papillomaviral infections: I. The anatomic distribution and pathologic grade of neoplastic lesions associated with different viral types" *Am. J. Obstet. Gynecol.* 156:212–222.

Scheffner, M., et al. (1990) "The E6 oncoprotein encoded by human papillomavirus types 16 and 18 promotes the degradation of p53" *Cell* 63:1129–1136.

Werness, B.A., et al. (1990) "Association of human papillomavirus types 16 and 18 E6 proteins with p53" *Science* 248:76–79.

FIGURE 3

| | | 10 | 20 | 30 | 40 | 50 | |
|---|---|---|---|---|---|---|---|
| HPV16 E6 AMP | 1 | GAGGTATATG | ACTTTGCTTT | TCGGGATTTA | TGCATAGTAT | ATAGAGATGG | 50 |
| HPV18 E6 AMP | 1 | GAGGTATTTG | AATTTGCATT | TAAAGATTTA | TTTGTGGTGT | ATAGAGACAG | 50 |
| HPV31 E6 AMP | 1 | GAGGTATTAG | ATTTTGCATT | TACAGATTTA | ACAATAGTAT | ATAGGGACGA | 50 |
| HPV33 E6 AMP | 1 | GAGGTATATG | ATTTTGCATT | TGCAGATTTA | ACAGTTGTAT | ATAGAGAGGG | 50 |
| HPV35 E6 AMP | 1 | GAGGTATATG | ACTTTGCATG | CTATGATTTG | TGTATAGTAT | ATAGAGAAGG | 50 |
| HPV39 E6 AMP | 1 | GAGGTATATG | AATTTGCATT | TAGTGATTTA | TATGTAGTAT | ATAGGGACGG | 50 |
| HPV45 E6 AMP | 1 | GAGGTATATC | AATTTGCTTT | TAAAGATTTA | TGTATAGTGT | ATAGAGACTG | 50 |
| HPV56 AMP | 1 | GAGGTATATA | ATTTTGCATG | CACTGAATTA | AAATTAGTGT | ATAGGGATGA | 50 |
| HPV58 E6 AMP | 1 | GAGGTATATG | ACTTTGTATT | TGCAGATTTA | AGAATAGTGT | ATAGAGATGG | 50 |

| | | 60 | 70 | 80 | 90 | 100 | |
|---|---|---|---|---|---|---|---|
| HPV16 E6 AMP | 51 | GAATCCATAT | GCTGTATGTG | ATAAATGTTT | AAAGTTTTAT | TCTAAAATTA | 100 |
| HPV18 E6 AMP | 51 | TATACCCCAT | GCTGCATGCC | ATAAATGTAT | AGATTTTTAT | TCTAGAATTA | 100 |
| HPV31 E6 AMP | 51 | CACACCACAC | GGAGTGTGTA | CAAAATGTTT | AAGATTTTAT | TCAAAAGTAA | 100 |
| HPV33 E6 AMP | 51 | AAATCCATTT | GGAATATGTA | AACTGTGTTT | GCGGTTCTTA | TCTAAAATTA | 100 |
| HPV35 E6 AMP | 51 | CCAGCCATAT | GGAGTATGCA | TGAAATGTTT | AAAATTTTAT | TCAAAAATAA | 100 |
| HPV39 E6 AMP | 51 | GGAACCACTA | GCTGCATGCC | AATCATGTAT | AAAATTTTAT | GCTAAAATAC | 100 |
| HPV45 E6 AMP | 51 | TATAGCATAT | GCTGCATGCC | ATAAATGTAT | AGACTTTTAT | TCCAGAATTA | 100 |
| HPV56 AMP | 51 | TTTTCCTTAT | GCAGTGTGCA | GAGTATGTTT | ATTGTTTTAT | AGTAAAGTTA | 100 |
| HPV58 E6 AMP | 51 | AAATCCATTT | GCAGTATGTA | AAGTGTGCTT | ACGATTGCTA | TCTAAAATAA | 100 |

| | | 110 | 120 | 130 | 140 | 150 | |
|---|---|---|---|---|---|---|---|
| HPV16 E6 AMP | 101 | GTGAGTATAG | ACATTATTGT | TATAGTTTGT | ATGGAACAAC | ATTAGAACAG | 150 |
| HPV18 E6 AMP | 101 | GAGAATTAAG | ACATTATTCA | GACTCTGTGT | ATGGAGACAC | ATTGGAAAAA | 150 |
| HPV31 E6 AMP | 101 | GTGAATTTAG | ATGGTATAGA | TATAGTGTGT | ATGGAACAAC | ATTAGAAAAA | 150 |
| HPV33 E6 AMP | 101 | GTGAATATAG | ACATTATAAT | TATTCTGTAT | ATGGAAATAC | ATTAGAACAA | 150 |
| HPV35 E6 AMP | 101 | GTGAATATAG | ATGGTATAGA | TATAGTGTGT | ATGGAGAAAC | GTTAGAAAAA | 150 |
| HPV39 E6 AMP | 101 | GGGAGCTACG | ATATTACTCG | GACTCGGTGT | ATGCAACTAC | ATTAGAAAAT | 150 |
| HPV45 E6 AMP | 101 | GAGAATTAAG | ATATTATTCA | AACTCTGTAT | ATGGAGAGAC | ACTGGAAAAA | 150 |
| HPV56 AMP | 101 | GAAAATATAG | GTATTATGAC | TATTCAGTGT | ATGGAGCTAC | ACTAGAAAGT | 150 |
| HPV58 E6 AMP | 101 | GTGAGTATAG | ACATTATAAT | TATTCGCTAT | ATGGAGACAC | ATTAGAACAA | 150 |

| | | 160 | 170 | 180 | 190 | 200 | |
|---|---|---|---|---|---|---|---|
| HPV16 E6 AMP | 151 | CAATACAACA | AACCGTTGTG | TGATTTGTTA | ATTAGGTG.. | .......... | 200 |
| HPV18 E6 AMP | 151 | CTAACTAACA | CTGGGTTATA | CAATTTATTA | ATAAGGTG.. | .......... | 200 |
| HPV31 E6 AMP | 151 | TTGACAAACA | AAGGTATATG | TGATTTGTTA | ATTAGGTG.. | .......... | 200 |
| HPV33 E6 AMP | 151 | ACAGTTAAAA | AACCTTTAAA | TGAAATATTA | ATTAGGTG.. | .......... | 200 |
| HPV35 E6 AMP | 151 | CAATGCAACA | AACAGTTATG | TCATTTATTA | ATTAGGTG.. | .......... | 200 |
| HPV39 E6 AMP | 151 | ATAACTAATA | CAAAGTTATA | TAATTTATTA | ATAAGGTG.. | .......... | 200 |
| HPV45 E6 AMP | 151 | ATAACTAATA | CAGAGTTGTA | TAATTTGTTA | ATAAGGTG.. | .......... | 200 |
| HPV56 AMP | 151 | ATAACTAAAA | AACAGTTATG | TGATTTATTA | ATAAGGTG.. | .......... | 200 |
| HPV58 E6 AMP | 151 | ACACTAAAAA | AGTGTTTAAA | TGAAATATTA | ATTAGATG.. | .......... | 200 |

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear -continued (ii) MOLECULE TYPE: DNA (genomic)

(iii) HYPOTHETICAL: NO (iv) ANTI-SENSE: NO (xi) SEQUENCE DESCRIPTION: SEQ ID NO:1:

GAGATTTATT CATACT    16

(2) INFORMATION FOR SEQ ID NO:2:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

GTGGCTTAAT CGTGCA    16

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

GAGATATATG CATATG    16

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GTTGCTTAAT TGTGAA    16

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO ( i v ) ANTI-SENSE: NO ( x i ) SEQUENCE DESCRIPTION: SEQ ID NO:5:

GAGGTATATG ACTTTG 16

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GTGGATTAAT TGTTTA 16

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

GAGGTATTTG AATTTG 16

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

GTGGAATAAT TATTTA 16

( 2 ) INFORMATION FOR SEQ ID NO:9:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GAGGTATATA ATTTTG 16

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

GTGGAATAAT TATTTA 16

(2) INFORMATION FOR SEQ ID NO:11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

GAGGTATTAG ATTTTG 16

(2) INFORMATION FOR SEQ ID NO:12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

GTGGATTAAT TGTTTA 16

(2) INFORMATION FOR SEQ ID NO:13:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

GAAGCGTATG CATATC 16

(2) INFORMATION FOR SEQ ID NO:14:

( i ) SEQUENCE CHARACTERISTICS:
   ( A ) LENGTH: 16 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

GTCGCTTAAT AAACAA                                                16

( 2 ) INFORMATION FOR SEQ ID NO:15:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

GAGGTATATG ATTTTG                                                16

( 2 ) INFORMATION FOR SEQ ID NO:16:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

GTGGATTAAT TATAAA                                                16

( 2 ) INFORMATION FOR SEQ ID NO:17:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

GAGGTATATG ATTTTA                                                16

( 2 ) INFORMATION FOR SEQ ID NO:18:

( i ) SEQUENCE CHARACTERISTICS:
      ( A ) LENGTH: 16 base pairs
      ( B ) TYPE: nucleic acid (C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

GTGGAATAAT TTTATA 16

(2) INFORMATION FOR SEQ ID NO:19:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

GAGGTATATG ACTTTG 16

(2) INFORMATION FOR SEQ ID NO:20:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

GTGGATTAAT TATTTA 16

(2) INFORMATION FOR SEQ ID NO:21:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

GAGGTATATG AATTTG 16

(2) INFORMATION FOR SEQ ID NO:22:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ii) MOLECULE TYPE: DNA (genomic)

(i i i) HYPOTHETICAL: NO (i v) ANTI-SENSE: NO (x i) SEQUENCE DESCRIPTION: SEQ ID NO:22:

GTGGAATAAT TATTTA  16

(2) INFORMATION FOR SEQ ID NO:23:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:23:

GAGGTGCTCG CGTACC  16

(2) INFORMATION FOR SEQ ID NO:24:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:24:

GTAGATTAAA CAACAA  16

(2) INFORMATION FOR SEQ ID NO:25:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:25:

GAGGTATATC AATTTG  16

(2) INFORMATION FOR SEQ ID NO:26:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO ( x i ) SEQUENCE DESCRIPTION: SEQ ID NO:26:

GTGGAATAAT TGTTTA                    16

( 2 ) INFORMATION FOR SEQ ID NO:27:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

GATGTATATA ATGTAG                    16

( 2 ) INFORMATION FOR SEQ ID NO:28:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:28:

GTGGAATAGC TATTTA                    16

( 2 ) INFORMATION FOR SEQ ID NO:29:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:29:

GAGGTATACA AGTTTC                    16

( 2 ) INFORMATION FOR SEQ ID NO:30:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:30:

GTAGATTATC AATAAA                    16

( 2 ) INFORMATION FOR SEQ ID NO:31:

( i ) SEQUENCE CHARACTERISTICS:
           ( A ) LENGTH: 16 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:31:

GAGGTATATA ATTTTG           16

( 2 ) INFORMATION FOR SEQ ID NO:32:

( i ) SEQUENCE CHARACTERISTICS:
           ( A ) LENGTH: 16 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:32:

GTGGAATAAC TATTTA           16

( 2 ) INFORMATION FOR SEQ ID NO:33:

( i ) SEQUENCE CHARACTERISTICS:
           ( A ) LENGTH: 16 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:33:

GAGGTATATA ATTTTG           16

( 2 ) INFORMATION FOR SEQ ID NO:34:

( i ) SEQUENCE CHARACTERISTICS:
           ( A ) LENGTH: 16 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:34:

GTGGAATAAT TATTTA           16

( 2 ) INFORMATION FOR SEQ ID NO:35:

```
       ( i ) SEQUENCE CHARACTERISTICS:
              ( A ) LENGTH: 16 base pairs
              ( B ) TYPE: nucleic acid
              ( C ) STRANDEDNESS: single
              ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:35:
```

GAGGTATATG ACTTTG                                                                                          16

( 2 ) INFORMATION FOR SEQ ID NO:36:

```
       ( i ) SEQUENCE CHARACTERISTICS:
              ( A ) LENGTH: 16 base pairs
              ( B ) TYPE: nucleic acid
              ( C ) STRANDEDNESS: single
              ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:36:
```

GTAGATTAAT TATAAA                                                                                          16

( 2 ) INFORMATION FOR SEQ ID NO:37:

```
       ( i ) SEQUENCE CHARACTERISTICS:
              ( A ) LENGTH: 16 base pairs
              ( B ) TYPE: nucleic acid
              ( C ) STRANDEDNESS: single
              ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:37:
```

GAGGTATATA ATTTTG                                                                                          16

( 2 ) INFORMATION FOR SEQ ID NO:38:

```
       ( i ) SEQUENCE CHARACTERISTICS:
              ( A ) LENGTH: 16 base pairs
              ( B ) TYPE: nucleic acid
              ( C ) STRANDEDNESS: single
              ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:38:
```

GTGGAATAAT TATTTA                                                                                          16

( 2 ) INFORMATION FOR SEQ ID NO:39:

```
       ( i ) SEQUENCE CHARACTERISTICS:
              ( A ) LENGTH: 18 base pairs
              ( B ) TYPE: nucleic acid
              ( C ) STRANDEDNESS: single
```

(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:39:

AAGTTGACAA CAACGTAT 18

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:40:

AAGATGACAT CCACGTAT 18

(2) INFORMATION FOR SEQ ID NO:41:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:41:

AAGATTACAA CAAGGTAT 18

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:42:

AAGGTTACAC AGAGGTAT 18

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(i i i) HYPOTHETICAL: NO (i v) ANTI-SENSE: NO (x i) SEQUENCE DESCRIPTION: SEQ ID NO:43:

GTGATCCGAA CGGGGTAT 18

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:44:

AAGATTACAA CAAGGTAT 18

(2) INFORMATION FOR SEQ ID NO:45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:45:

AAGATGACAT ACGGTTTT 18

(2) INFORMATION FOR SEQ ID NO:46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:46:

AAGATTACAT AAAGGTAT 18

(2) INFORMATION FOR SEQ ID NO:47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO ( x i ) SEQUENCE DESCRIPTION: SEQ ID NO:47:

GAGATTGCAG GCAGGTAT 18

( 2 ) INFORMATION FOR SEQ ID NO:48:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:48:

AAGATTGCAA AGAGGTAT 18

( 2 ) INFORMATION FOR SEQ ID NO:49:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:49:

AAGATTACAT CAACGTAT 18

( 2 ) INFORMATION FOR SEQ ID NO:50:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:50:

GAGGTGACAT ATGGTTTT 18

( 2 ) INFORMATION FOR SEQ ID NO:51:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:51:

AAGGTCACAG AGAGGTAT 18

( 2 ) INFORMATION FOR SEQ ID NO:52:

( i ) SEQUENCE CHARACTERISTICS:
           ( A ) LENGTH: 18 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:52:

GAGATTACAT CATGGTAT                                                                 18

( 2 ) INFORMATION FOR SEQ ID NO:53:

( i ) SEQUENCE CHARACTERISTICS:
           ( A ) LENGTH: 18 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:53:

AAGATTACAA AAGGGTAT                                                                 18

( 2 ) INFORMATION FOR SEQ ID NO:54:

( i ) SEQUENCE CHARACTERISTICS:
           ( A ) LENGTH: 18 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:54:

AAGGTCCGAT CGGGGCAT                                                                 18

( 2 ) INFORMATION FOR SEQ ID NO:55:

( i ) SEQUENCE CHARACTERISTICS:
           ( A ) LENGTH: 18 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:55:

AAGATCACAT CGAGGTAT                                                                 18

( 2 ) INFORMATION FOR SEQ ID NO:56:

( i ) SEQUENCE CHARACTERISTICS:

(A) LENGTH: 18 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:56:

AAGATTACAC AGAGGTAT                                                                 18

(2) INFORMATION FOR SEQ ID NO:57:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:57:

AAGATCACAT CGAGGTAT                                                                 18

DETECTION OF HIGH ONCOGENIC-RISK PAPILLOMA VIRUS IN HIGH GRADE CERVICAL LESIONS AND CANCERS BY A PCR/ELISA ASSAY

This application is a continuation of application of U.S. Ser. No. 08/390,684, filed Feb. 17, 1995, now abandoned.

Throughout this application, various publications are referenced by Arabic numerals in brackets. Full citations for these publications may be found at the end of the specification preceding the claims. The disclosures of these publications are in their entirety hereby incorporated by reference into this application to more fully describe the state of the art to which this invention pertains.

BACKGROUND OF THE INVENTION

It is now widely accepted that the majority of invasive cervical cancers and high grade cancer precursor lesions are associated with "high and to a lesser extent intermediate oncogenic-risk" types of HPV [1–4]. Despite the close association between the "high oncogenic-risk" HPV types and the development of cervical disease, testing for these viruses has not been incorporated in clinical practice. The reluctance to adopt HPV testing in clinical practice has been attributed to a number of factors including the lack of a specific, sensitive and easy to perform assay for detecting "high oncogenic-risk" HPVs. For example, in some clinical series over 50% of women with invasive cervical cancer have been HPV DNA negative using various HPV tests [5–8]. Moreover, other assays that have been used to identify "high oncogenic-risk" types of HPV such as Southern blot hybridization or PCR amplification followed by a dot blot or gel electrophoresis of the PCR products to identify amplified HPV sequences are frequently considered to be too complicated and expensive for routine clinical use [9, 10].

SUMMARY OF THE INVENTION

This invention provides a method of detecting a high oncogenic-risk type human papillomavirus in a subject which comprises: obtaining from a subject a specimen containing cervical cells and treating the specimen so as to recover nucleic acid molecules present in the cervical cells; contacting the resulting nucleic acid molecules with multiple pairs of single-stranded labeled oligonucleotide primers capable of specifically hybridizing with a different high oncogenic-risk type of human papillomavirus; amplifying any nucleic acid molecules to which a pair of primers hybridizes so as to obtain a double-stranded amplification product and treating any double-stranded amplification product so as to obtain single-stranded nucleic acid molecules; contacting any resulting single-stranded nucleic acid molecules with multiple single-stranded labeled oligonucleotide probes which are capable of specifically hybridizing with such high oncogenic-risk types of human papillomavirus; contacting any resulting hybrids with a marked antibody capable of specifically forming a complex with the labeled probe, when the probe is present in such a complex; and detecting the presence of any resulting complexes, the presence thereof being indicative of the presence of a high oncogenic-risk type human papillomavirus in the initial specimen.

The DNA is amplified by PCR with biotinylated 5' primers. The amplification products are captured on streptavidin coated plates, rendered single-stranded by denaturation and hybridized to a 5' fluorescein labeled probe. The hybridized probe is detected using an antifluorescein alkaline-phosphatase conjugated antibody and the signal measured in an ELISA reader. PNP refers to the paranitrophenyl substrate, OD is optical density, and FITC-AP refers to fluorescein-alkaline phosphatase conjugate.

Figure 2:
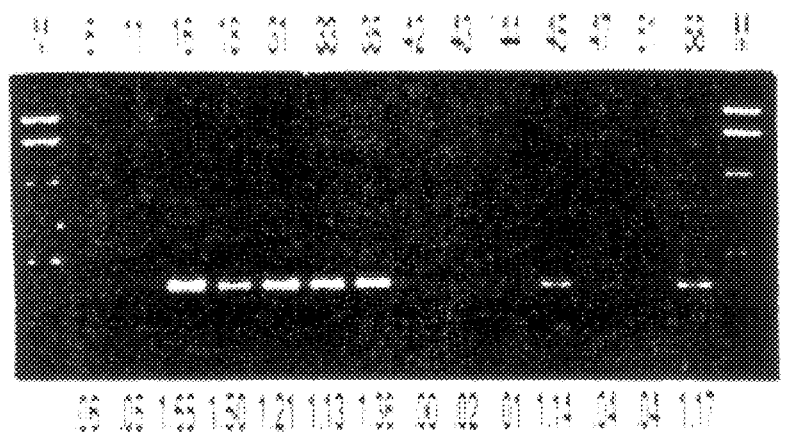

FIG. 2. PCR/ELISA analyzes of cloned HPV DNAs.

Five-hundred femtograms of cloned HPV DNAs were amplified by PCR. The amplified DNAs were then analyzed by agarose gel electrophoresis and ELISA as described in the specification. The numbers above the gel identify the types of HPV used in each reaction, and the numbers below represent the ELISA OD readings for each sample after amplification and hybridization. The marker lane contains 1.5 mg of MspI-digested pBR322 DNA.

FIG. 3. E6 Open Reading Frame Sequences for High Oncogenic-Risk Type Human Papillomaviruses.

Open reading frame sequences for the E6 oncoprotein in high oncogenic-risk human papillomaviruses are listed. These sequences are the target amplification sequences of the human papillomavirus primers.

DETAILED DESCRIPTION OF THE INVENTION

This invention provides a method of detecting a high oncogenic-risk type human papillomavirus in a subject which comprises: (a) obtaining from a subject a specimen containing cervical cells; (b) treating the specimen so as to separately recover nucleic acid molecules present in the cervical cells; (c) contacting the resulting nucleic acid molecules with multiple pairs of single-stranded labeled oligonucleotide primers, each such pair being capable of specifically hybridizing with a different high oncogenic-risk type of human papillomavirus, under hybridizing conditions; (d) amplifying any nucleic acid molecules to which a pair of primers hybridizes so as to obtain a double-stranded amplification product; (e) treating any such double-stranded amplification product so as to obtain single-stranded nucleic acid molecules therefrom; (f) contacting any resulting single-stranded nucleic acid molecules with multiple single-stranded labeled oligonucleotide probes, each such probe containing the same label and being capable of specifically hybridizing with such high oncogenic-risk types of human papillomavirus, under hybridizing conditions; (g) contacting any resulting hybrids with an antibody to which a marker is attached and which is capable of specifically forming a complex with the labeled-probe, when the probe is present in such a complex, under complexing conditions; and (h) detecting the presence of any resulting complexes, the presence thereof being indicative of the presence of a high oncogenic-risk type human papillomavirus in the initial specimen.

The method is based on polymerase chain reaction (PCR) amplification and enzyme-linked immunosorbent (ELISA) assay detection using consensus primers and a degenerate probe that specifically amplifies and detects high oncogenic-risk human papillomavirus types.

The PCR/ELISA human papillomavirus detection method provides the capability for automated, rapid and sensitive testing for determining cervical cancer and high grade cervical lesions.

Genital HPVs are common sexually transmitted agents that induce a variety of proliferative lesions. Infection by high oncogenic-risk types of HPV is the most significant risk factor for the development of cervical intraepithelial neoplasia and the progression to invasive cervical carcinomas [16].

As used herein, "high oncogenic-risk type HPVs" are those types of HPVs which are significant risk factors for the development of cervical carcinomas. Examples of high oncogenic-risk HPVs include but are not limited to HPV 16, HPV 18, HPV 31, HPV 33, HPV 35, HPV 39, HPV 45, HPV 56, HPV 58 and HPV 65. The presence of high oncogenic-risk type HPVs in a subject is predictive of developing cervical cancer or high grade cervical lesions.

As used herein "polymerase chain reaction/enzyme-linked immunosorbent (PCR/ELISA) assay" is the technique by which nucleic acid molecules are amplified by polymerase chain reaction in order to produce large amounts of specific nucleic acid products which can then be detected by the ELISA method. PCR/ELISA methods are known to those skilled in the art.

In the preferred embodiment, the HPV assay is based on PCR amplification of a region of the E6 open reading frame and ELISA detection of PCR products that specifically identifies "high oncogenic-risk" HPV types.

HPVs encode viral oncoproteins which bind to the products of tumor suppressor genes and are capable of transforming cells. The E6 open reading frame encoded in high oncogenic-risk HPV expresses the E6 oncoprotein and is contained in cancer cells intact [17].

A specimen containing cervical cells is obtained by swabs of the cervix of the subject. Methods of obtaining suitable cells from a subject are known to those skilled in the art.

The specimen containing cervical cells is treated so as to recover nucleic acid molecules in the cervical cells. Methods of recovering nucleic acids from a sample are known to those skilled in the art.

The phrase "nucleic acid molecule" refers to a nucleic acid molecule which directs the expression of a specific protein or peptide. The nucleic acid sequences include both the DNA strand sequence that is transcribed into RNA and the RNA sequence that is translated into protein. The nucleic acid molecules include both the full length nucleic acid sequences as well as non-full length sequences derived from the full length protein. It being further understood that the sequence includes the degenerate codons of the native sequence or sequences which may be introduced to provide codon preference in a specific host cell.

In one embodiment the nucleic acid molecules may be DNA, RNA, or cDNA molecules. In a preferred embodiment, the nucleic acid molecules are DNA molecules.

As used herein, "primers" indicate single-stranded labeled nucleic acid segments with free 3'—OH groups that function as growing points in polymerization reactions.

Oligonucleotides for use as PCR primers or as probes are chemically synthesized according to the solid phase phosphoramidite triester method first described by Beaucage and Carruthers [18] using an automated synthesizer, as described in Needham-VanDevanter [19]. Purification of oligonucleotides is by either native acrylamide gel electrophoresis or by anion-exchange HPLC as described in Pearson, J. D. and Regnier, F. E. [20]. The sequence of the synthetic oligonucleotide 4can be verified using the chemical degradation method of Maxam, A. M. and Gilbert, W. [21].

Polymerase chain reaction technology is based on the ability to amplify a specific DNA segment flanked by a set of primers. Primers define a target sequence for amplification and avoid the generation of false signals from other nucleic acid molecules present in samples. This allows for production of large amounts of specific DNA products, which can be detected by various methods. PCR amplification methods are known to those skilled in the art [22].

In a preferred embodiment, the multiple pairs of single-stranded labeled oligonucleotide primers are selected from a group consisting of the primers HPV 16, HPV 18, HPV 31, HPV 33, HPV 35, HPV 39, HPV 45, HPV 56, HPV 58, AND HPV 65.

In the preferred embodiment the single-stranded labeled oligonucleotide primers are labeled with biotin.

Human papillomavirus 5' primer and human papillomavirus 3' primer sequences (respectively) are as follows:

human papillomavirus 6 (SEQ ID NOs: 1 and 2),
human papillomavirus 11 (SEQ ID NOs: 3 and 4),
human papillomavirus 16 (SEQ ID NOs: 5 and 6),
human papillomavirus 18 (SEQ ID NOs: 7 and 8),
human papillomavirus 30 (SEQ ID NOs: 9 and 10),
human papillomavirus 31 (SEQ ID NOs: 11 and 12),
human papillomavirus 32 (SEQ ID NOs: 13 and 14),
human papillomavirus 33 (SEQ ID NOs: 15 and 16),
human papillomavirus 34 (SEQ ID NOs: 17 and 18),
human papillomavirus 35 (SEQ ID NOs: 19 and 20),
human papillomavirus 39 (SEQ ID NOs: 21 and 22),
human papillomavirus 42 (SEQ ID NOs: 23 and 24),
human papillomavirus 45 (SEQ ID NOs: 25 and 26),
human papillomavirus 51 (SEQ ID NOs: 27 and 28),
human papillomavirus 52 (SEQ ID NOs: 29 and 30),
human papillomavirus 53 (SEQ ID NOs: 31 and 32),
human papillomavirus 56 (SEQ ID NOs: 33 and 34),
human papillomavirus 58 (SEQ ID NOs: 35 and 36), and
human papillomavirus 65 (SEQ ID NOs: 37 and 38).

The nucleic acid molecules obtained from suitable cells are amplified by the polymerase chain reaction method. In one embodiment multiple pairs of single-stranded oligonucleotide primers are contacted with the resulting nucleic acid to produce an amplification product. Each pair of single-stranded oligonucleotide primers is capable of specifically hybridizing with a different high oncogenic-risk type of human papillomavirus under hybridizing conditions.

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. For Example high stringency may be attained for example by overnight hybridization at about 68° C. in a 6×SSC solution, washing at room temperature with 6×SSC solution, followed by washing at about 68° C. in a 6×SSC in a 0.6×SSX solution.

Hybridization with moderate stringency may be attained for example by: 1) filter pre-hybridizing and hybridizing with a solution of 3×sodium chloride, sodium citrate (SSC), 50% formamide, 0.1M Tris buffer at Ph 7.5, 5×Denhardt's solution; 2.) pre-hybridization at 37° C. for 4 hours; 3) hybridization at 37° C. with amount of labeled probe equal to 3,000,000 cpm total for 16 hours; 4) wash in 2×SSC and 0.1% SDS solution; 5) wash 4× for 1 minute each at room temperature at 4× at 60° C. for 30 minutes each; and 6 dry and expose to film.

In one embodiment the nucleic acid molecule is amplified within a region of the E6 open reading frame. Any nucleic acid molecules hybridized to a pair of primers is amplified to produce an amplification product. Amplification is performed by repeated cycles of denaturing, annealing and extension. Methods of amplification are known to those skilled in the art.

The products of the amplification reactions are then transferred to coated plates. In a preferred embodiment, the plates are coated with streptavidin. Methods of capturing the double-stranded amplification product are known to those skilled in the art.

The double-stranded amplification product is then denatured so as to obtain single-stranded nucleic acid molecules. Methods of denaturing double-stranded amplification product are known to those skilled in the art.

As used herein, "probes" are synthetic or isolated nucleic acid molecules used in hybridization assays.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the human papillomavirus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

The single-stranded nucleic acid is contacted with multiple single-stranded labeled oligonucleotide probes. Each probe selected is capable of specifically hybridizing with high oncogenic-risk types of human papillomavirus. The presence of a specific nucleic acid sequence can be detected by using a labeled complementary nucleic acid molecule as a probe. In one embodiment, the specific human papillomavirus probes are selected from a group consisting of the probes HPV 16, HPV 18, HPV 31, HPV 33, HPV 35, HPV 39, HPV 45, HPV 56, HPV 58, AND HPV 65. Methods of hybridizing nucleic acids with probes are known to those skilled in the art.

In one embodiment the single-stranded labeled oligonucleotide probes are labeled with a fluorescent or radioactive label. In the preferred embodiment the label is fluorescein.

Human papillomavirus probe sequences are as follows:
human papillomavirus 6 (SEQ ID NO: 39),
human papillomavirus 11 (SEQ ID NO: 40),
human papillomavirus 16 (SEQ ID NO: 41),
human papillomavirus 18 (SEQ ID NO: 42),
human papillomavirus 30 (SEQ ID NO: 43),
human papillomavirus 31 (SEQ ID NO: 44),
human papillomavirus 32 (SEQ ID NO: 45),
human papillomavirus 33 (SEQ ID NO: 46),
human papillomavirus 34 (SEQ ID NO: 47),
human papillomavirus 35 (SEQ ID NO: 48),
human papillomavirus 39 (SEQ ID NO: 49),
human papillomavirus 42 (SEQ ID NO: 50),
human papillomavirus 45 (SEQ ID NO: 51),
human papillomavirus 51 (SEQ ID NO: 52),
human papillomavirus 52 (SEQ ID NO: 53),
human papillomavirus 53 (SEQ ID NO: 54),
human papillomavirus 56 (SEQ ID NO: 55),
human papillomavirus 58 (SEQ ID NO: 56), and
human papillomavirus 65 (SEQ ID NO: 57).

The resulting hybrids are then contacted with a detectably marked antibody. The antibody may be labeled with a detectable marker including, but not limited to: a radioactive label, or a calorimetric, a luminescent, or a fluorescent marker, or gold. Radioactive labels include, but are not limited to: $^{3}H$, $^{14}C$, $^{32}P$, $^{33}P$; $^{35}S$, $^{36}Cl$, $^{51}Cr$, $^{57}Co$, $^{59}CO$, $^{59}Fe$, $^{90}Y$, $^{125}I$, $^{131}I$, and $^{186}Re$. Fluorescent markers include but are not limited to: fluorescein, rhodamine and auramine. Colorimetric markers include, but are not limited to: biotin, and digoxigenin. In the preferred embodiment, the antibody is marked with alkaline phosphatase.

Further, the antibody or nucleic acid molecule complex may be detected by a second antibody which may be linked to an enzyme, such as alkaline phosphatase or horseradish peroxidase. Other enzymes which may be employed are known to those skilled in the art.

The presence of any resulting complexes is then detected by measuring qualitatively or quantitatively to determine high oncogenic-risk types of HPVs in the initial specimen. In one embodiment the measuring of the presence of high oncogenic-risk types of HPVs is performed in a qualitative manner. In another embodiment the measuring of the presence of high oncogenic-risk types of HPVs is performed in a quantitative manner. For example, one may employ ELISA, RIA, or colorimetric enzyme techniques which are known to those skilled in the art. In a preferred embodiment, the presence of high oncogenic-risk type HPVs is detected by ELISA techniques using optical density reading. In the preferred embodiment, the optical density is determined at 405 nm. Other methods of determining the presence of antibody are known to those skilled in the art.

In a preferred embodiment, the PCR/ELISA assay method of detecting a high oncogenic-risk type human papillomavirus in a subject further comprises performing a Papanicolaou (Pap) test on the specimen.

In a Pap test, a specimen is viewed under a microscope to determine whether the sample is normal or whether it shows signs of dysplasia or carcinoma. The methods of performing the Pap test are known to those skilled in the art.

In one embodiment, where complexes are detected which indicate the presence of high oncogenic-risk type human papillomavirus in a specimen, the double-stranded amplification products of the polymerase chain reaction are analyzed to determine the identity of the type of human papillomavirus present in the initial specimen. In one embodiment, the double-stranded amplification products are analyzed by gel electrophoresis. Methods of gel electrophoresis are known to those skilled in the art.

This invention is further illustrated in the Experimental Details section which follows. This section is set forth to aid in an understanding of the invention but is not intended to, and should not be construed to, limit in any way the invention as set forth in the claims which follow thereafter.

Experimental Details

I. Methods

A) PCR/ELISA Assay

Figure 1:
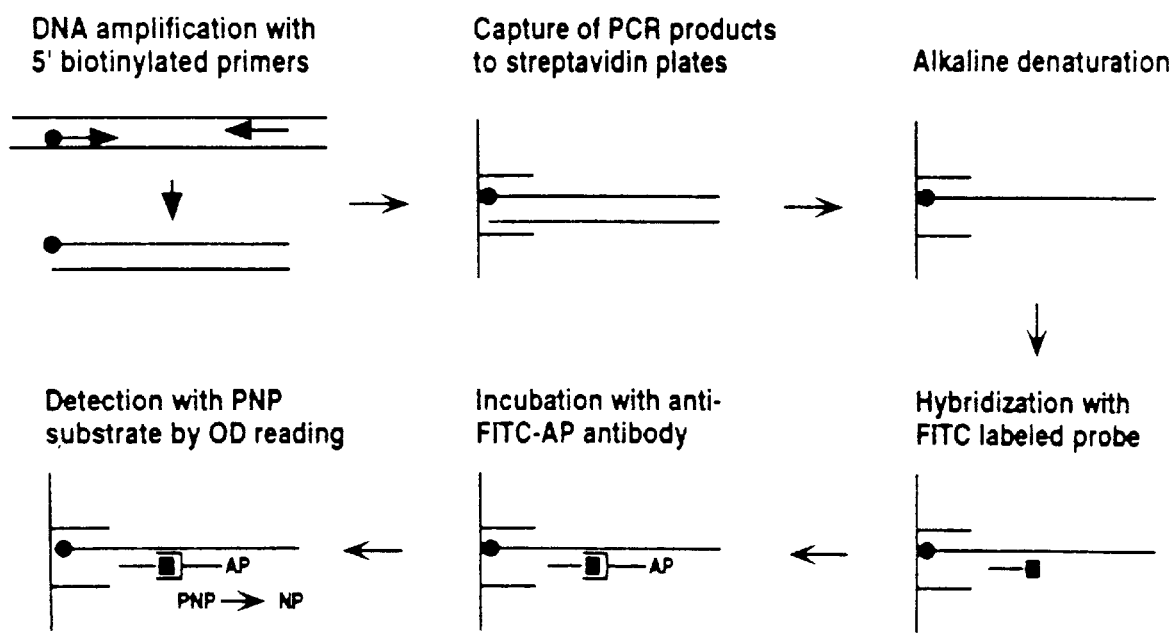
FIG. 1. Outline of the PCR/ELISA Assay.

The PCR/ELISA procedure is summarized in FIG. 1. A region of the E6 open reading frame was chosen as the target for amplification because the E6 gene product is implicated in human papillomavirus carcinogenesis and therefore this oncogene should be present in all HPV related cervical carcinomas and high grade precursors [11, 12]. Alignment of the DNA sequences encoding E6 from different HPV types, as presented in Table 1, permitted us to identify amplification primers and a detection probe that will specifically recognize "high oncogenic-risk" HPV sequences. As shown in Table 1 the primers and/or the probe selected have sequences that are homologous or have only a single nucleotide mismatch with sequences of HPV types 16, 18, 31, 33, 35, 39, 45, 56, 58 and 65 whereas multiple nucleotide mismatches are present between the selected primers and/or probe sequences and HPV types 6, 11, 30, 32, 34, 42, 51, 52 and 53. Cloned "high oncogenic-risk" and "low oncogenic-risk" DNAs from HPV types 6, 11, 16, 18, 31 33, 35, 42, 43, 44, 45, 47, 51 and 58 were used to determine the amplification and detection conditions that identify only HPV types with sequences that are homologous to, or have a single nucleotide mismatch with the selected primers and probe sequences. These conditions are as follows.

Amplification is performed for 38 cycles of denaturing at 94° C. for 1 min., annealing at 42° C. for 1.5 min. and extension at 72° C. for 1 min. in a 100 mL reaction containing 50 mM KCl, 1.5 mM MgCl$_2$, 10 mM Tris pH 8.5, 200 mM dNTPs, 1 mM spermidine, 120 pmoles of 5'-biotin-GAGGTAT (A/T)TGAITTTG-3' primer, 60 pmoles of 5'-biotin-GAGGTATATGACTTTG-3', 5'-CACCTAATTAACAAAT-3', 5'-CACCTTATTAATAAAT-3' and 5'-CACCTAATTAATATTT-3'primers (Operon Technologies Inc., Alameda Calif.) and 2.5 U of Taq DNA polymerase. For HPV detection, 50 mL of the amplification reactions are transferred to streptavidin coated plates (Pierce, Rockford Ill.) containing 50 ml of hybridization buffer (5×SSC, 1% BSA and 1% Triton×100). The plates are then incubated at room temperature for 30 min. and washed once with 200 ml of washing buffer (25 mM Tris pH 7.4, 150 mM NaCl, 0.1% BSA and 0.05% Tween 20). The captured double-stranded amplified DNA is than denatured in 100 ml of 0.5M NaOH at room temperature for 5 min. After 2 washes, 100 mL of hybridization buffer containing 25 pmoles of fluorescein labeled probe, 5'-fluorescein-TTC(C/T)AATGTI(G/T)(C/T)TCCATA-3' (Operon Technologies Inc., Alameda Calif.), are added and the plates incubated at room temperature for 60 min The plates are then washed 3 times with 200 mL of wash buffer, and 100 mL of hybridization buffer containing 1/4000 dilution of anti-fluorescein-alkaline phosphatase conjugated antibodies (Boehringer Mannheim, Indianapolis Ind.) are added. After 30 min. incubation at room temperature the plates are washed 4 times to remove the excess antibodies and 100 mL of alkaline phosphatase buffer (100 mM Tris pH 9.5, 100 mM NaCl, 5 MM MgCl$_2$) containing 1 mg/mL of paranitrophenyl (PNP) substrate are added. The optical density at 405 nm is determined after 1 hour incubation at room temperature.

B) Gel Electrophoresis Analysis of Amplified DNAs

DNA amplification products were analyzed by electrophoresis at 100 V in a 3.5% 5/1 Nu Sieve/Sea Plaque GTG agarose gel containing 0.2 mg/mL of ethidium bromide prepared in Tris-Borate buffer.

C) Clinical Sample Analysis

Dacron swabs were firmly wiped across the cervix of 371 women referred to the colposcopy clinic at Columbia Presbyterian Medical Center or the Sir Mortimer B. Davis Jewish General Hospital for either the evaluation of an abnormal Papanicolaou smear or of genital warts. Swabs were placed into ViraPap TM specimen collection tubes and stored at 4° C. until analysis. All women underwent colposcopy and had a repeat Papanicolaou test and a cervical biopsy. The repeat Papanicolaou test and cervical biopsies were routinely diagnosed at the two institutions and the clinical diagnosis was used for this study. The PCR amplification and the ELISA detection were performed in a blinded manner in two different laboratories. Negative controls were included with each amplification. To determine the specific HPV types present, most clinical samples were also analyzed by PCR/RFLP analysis as previously described [10, 13].

For PCR, 100 mL of the ViraPap TM transport media was pelleted using a microfuge, washed with 500 mL of 70% ethanol, and the DNA extracted by overnight digestion with Proteinase K (20 mg/ml) in 100 mL of buffer (50 mM Tris HCl pH 8.5, 1 mM EDTA, 0.5 mM Tween 20). The Proteinase K was then inactivated by boiling the sample for 10 min. after the addition of 5% Chelex-100. Twenty mL of the sample were used in the PCR reaction.

II. Results

The results of gel electrophoresis analysis of PCR amplification products from cloned HPV DNAs and the corresponding PCR/ELISA readouts from the same DNA samples are shown in FIG. 2. As predicted by sequence alignment analyses only "high oncogenic-risk" cloned HPV types were identified by the PCR/ELISA test. Ten to 100 femtograms of plasmid DNA from HPV types 16, 18, 31, 33, 35, 43, 45 and 58 could be amplified and detected by this assay, however, types 6, 11, 42, 44, 47 and 51 were not identified even when 10 ng of plasmid DNA were used as template for amplification. Interestingly, although the E6 and E7 ORFs of HPV 51 contain the conserved amino acids required for interaction with p53 and pRB105 [14] this virus is only rarely found in invasive cervical carcinomas [15] and is not amplified or detected using the primer pairs and probe described in this study.

The HPV test results, the Papanicolaou test results and the correlation between these results and the histologic findings in the 371 clinical samples analyzed are summarized in Table 2. The samples were obtained from seven women with histologically identified invasive cervical carcinomas, 81 women with high grade SIL, 128 women with low grade SIL, and 155 women with no evidence of cervical disease on either colposcopy or cervical biopsy. "High oncogenic-risk" HPVs were detected by the PCR/ELISA method in 6 of 7 (85%) carcinomas, 74 of 81 (91%) high grade lesions, 58 of 128 (45%) low grade lesions and 46 of 155 (29%) cases with normal pathology. The Papanicolaou test was abnormal in all 7 carcinomas, 71 of 81 (87%) high grade lesions, 84 of 128 (65%) low grade lesions and 36 of 155 (23%) histologically negative cases. All carcinomas, 79 of 81 (97%) high grade lesions, 100 of 128 (78%) low grade lesions and 65 of 155 (41%) samples from patients without histologically identified cervical pathology were positive when both the Papanicolaou and PCR/ELISA tests were used. To measure the reproducibility of the PCR/ELISA method, 50 samples were tested twice at an interval of 3 months. These samples included 25 HPV positive and 25 HPV negative specimens as determined by the initial testing. Forty-eight (96%) of these samples had concordant results between the initial test and the repeated analysis.

The specific HPV types detected by the PCR/ELISA test in the 229 clinical samples were determined using Hae III, Pst I and Rsa I restriction fragment length polymorphism analysis of the L1 amplification products as previously described [10, 13]. The results of this analysis are compiled in Table 3. One hundred fifty two samples were positive and 77 were negative by the PCR/ELISA assay while the PCR/

RFLP test identified HPVs in 224 of 229 samples. Of the 152 PCR/ELISA positive samples the PCR/ELISA assay detected high risk HPVs in 121 samples and low risk viruses in 4 samples. The virus type in 26 of the PCR/ELISA positive could not be determined by PCR/RFLP and 4 samples were negative. Of the 77 PCR/ELISA negative samples 17 were positive for high risk HPVs, 31 were positive for low risk HPVs, the virus type could not be determined in 25 samples and 4 were negative by the PCR/RFLP assay. The HPV types that were present in the PCR-ELISA positive samples were 16, 18, 31, 33, 35, 43/45, 56 and 58 and two "novel" types designated X2 and X6 [10].

These were the only types of viruses detected in cervical carcinomas and high grade cervical lesions. Other HPV types such as 6, 11, 44, 51, 53, and "novel" types designated X4, X9 and X10 detected by PCR-RFLP analyses in low grade and histologically normal samples were not identified by the PCR-ELISA test. Of the 17 samples positive for high risk HPVs by the PCR/RFLP method that were negative by PCR/ELISA one sample positive for HPV 6 and 31 was diagnosed as high grade squamous intraepithelial lesions (SIL) by histologic examination, while the other 16 samples show no histologic evidence of cervical disease or were diagnosed as low grade SIL by histology.

The results of this study using the PCR/ELISA method in 371 women with cervical carcinomas, high and low grade precursor lesions and without histologic evidence of cervical disease indicate that the PCR/ELISA assay is a sensitive and specific test for the identification of women with cervical carcinomas and high grade precursor lesions. The PCR/RFLP typing results indicate that only "high oncogenic-risk" HPV types are identified using the PCR/ELISA method. The finding that the PCR/ELISA test identified "high oncogenic-risk" HPVs in 8 of the 10 women in this study who had a high grade SIL but whose repeat Papanicolaou test was diagnosed as within normal limits suggests a potential role for HPV testing in the evaluation of these women.

The PCR/ELISA test was positive in only a small number (8% of the total) of women who had both a negative Papanicolaou test and no evidence of cervical disease on cervical biopsy. The HPV PCR/ELISA assay has a number of advantages over other PCR methodologies in that it is relatively simple to perform and can be automated completely. The method allows a large number of samples to be analyzed simultaneously and because the results are obtained with an ELISA reader they are less dependent upon subjective interpretation then those obtained with other methods such as dot blot hybridization of PCR products with radiolabeled probes.

TABLE 1

Alignment of Sequences From "High and Low Oncogenic-Risk" HPV Types With Primers and Probe Sequences Used in the PCR/ELISA Assay

| Type | 5' Sequence | Probe Sequence | 3' Sequence |
|---|---|---|---|
| HPV 6 | GAGATTTATTCATACT | TATGCAACAACAGTTGAA | ACGTGCTAATTCGGTG |
| HPV11 | GAGATATATGCATATG | TATGCACCTACAGTAGAA | AAGTGTTAATTCGTTG |
| HPV16 | GAGGTATATGACTTTG | TATGGAACAACATTAGAA | ATTTGTTAATTAGGTG |
| HPV18 | GAGGTATTTGAATTTG | TATGGAGACACATTGGAA | ATTTATTAATAAGGTG |
| HPV30 | GAGGTATATAATTTTG | TATGGGGCAAGCCTAGTG | ATTTATTAATAAGGTG |
| HPV31 | GAGGTATTAGATTTTG | TATGGAACAACATTAGAA | ATTTGTTAATTAGGTG |
| HPV32 | GAAGCGTATGCATATC | TTTTGGCATACAGTAGAA | AACAAATAATTCGCTG |
| HPV33 | GAGGTATATGATTTTG | TATGGAAATACATTAGAA | AAATATTAATTAGGTG |
| HPV34 | GAGGTATATGATTTTA | TATGGACGGACGTTAGAG | ATATTTTAATAAGGTG |
| HPV35 | GAGGTATATGACTTTG | TATGGAGAAACGTTAGAA | ATTTATTAATTAGGTG |
| HPV39 | GAGGTATATGAATTTG | TATGCAACTACATTAGAA | ATTTATTAATAAGGTG |
| HPV42 | GAGGTGCTCGCGTACC | TTTTGGTATACAGTGGAG | AACAACAAATTAGATG |
| HPV45 | GAGGTATATCAATTTG | TATGGAGAGACACTGGAA | ATTTGTTAATAAGGTG |
| HPV51 | GATGTATATAATGTAG | TATGGTACTACATTAGAG | ATTTATCGATAAGGTG |
| HPV52 | GAGGTATACAAGTTTC | TATGGGAAAACATTAGAA | AAATAACTATTAGATG |
| HPV53 | GAGGTATATAATTTTG | TACGGGGCTAGCCTGGAA | ATTTATCAATAAGGTG |
| HPV56 | GAGGTATATAATTTTG | TATGGAGCTACACTAGAA | ATTTATTAATAAGGTG |
| HPV58 | GAGGTATATGACTTTG | TATGGAGACACATTAGAA | AAATATTAATTAGATG |
| HPV65 | GAGGTATATAATTTTG | TATGGAGCTACACTAGAA | ATTTATTAATAAGGTG |
| Primers and Probe[1] | GAGGTATATGACTTTG GAGGTATWTGAITTTG | TATGGARMIACATTRGAA | ATTTGTTAATTAGGTG ATTTATTAATAAGGTG AAATATTAATTAGGTG |
| Position | 224–239 | 353–370 | 396–411 |

[1]Primer sequences correspond to the strand from which they are derived. Thus the 5' sequence is read in the 5'-3' direction whereas the 3' sequence, which is derived from the opposite strand is read in the 3'-5' direction. The probe sequence is complementary to the 5' strand and therefore is read in the same orientation (ie 3'-5') as the 3' sequence.
Note: Mismatches between primers/probe sequences and HPV sequences are in bold type. The positions were determined according to the published sequence of HPV16 DNA. The amplification product is 188 bp for all the above HPV types.
W denotes—A + T, I—Inosine, R—A + G, and M—A + C.

TABLE 2

Correlation of PCR/ELISA and Papanicolaou Smear Results With the Histologic Findings.

|  | Biopsy diagnosis | | | |
| --- | --- | --- | --- | --- |
|  | Carcinoma | High grade lesions | Low grade lesions | No histological detection of cervical disease |
|  | | No. of samples | | |
|  | 7 | 81 | 128 | 155 |
| PCR/ELISA+ | 6 | 74 | 58 | 46 |
| Pap+ | 7 | 71 | 84 | 36 |
| PCR/ELISA and/or Pap+ | 7 | 79 | 100 | 65 |

TABLE 3

Comparison of HPV Types Detected by the PCR/ELISA and PCR/RFLP Assays

|  | PCR/ELISA | | |
| --- | --- | --- | --- |
| PCR/RFLP Virus Type | Positive 152 | Negative 77 | Total 229 |
| High Risk | 121 | 17 | 138 |
| Low Risk | 4 | 31 | 35 |
| Undetermined | 26 | 25 | 51 |
| Negative | 1 | 4 | 5 |

REFERENCES

1. Gissman L. and Schneider A. (1986) "HPV DNA in preneoplastic and neoplastic genital lesions" *Viral Etiology of Cancer* (Peto R, zurHausen H. 217–24) Cold Spring Harbor, N.Y.: Cold Spring Harbor Laboratory.
2. Lorincz, A. T., et al. (1987) "Oncogenic association of specific HPV types with cervical neoplasia" *J. Natl. Cancer Inst.* 79:671–7.
3. Reid R., et al. (1987) "Sexually transmitted papillomaviral infections, I: the anatomic distribution and pathologic grade of neoplastic lesions associated with different viral types" *Am. J. Obstet. Gynecol.* 156:212–22.
4. Wright T. C. and Richart R. M. (1990) "Role of HPV in pathogenesis of genital tract warts and cancer" *Gynecol. Oncol.* 37:151–64.
5. Schmauz, R., et al. (1989) "Multiple infections in cases of cervical cancer from a high-incidence area in tropical Africa" *Int. J. Cancer* 43:805–9.
6. Donnan, S. P. B., et al. (1989) "Reproductive and sexual risk factors and HPV infection in cervical cancer among Hong Kong Chinese" *Int. J. Epidemiol.* 18:32–6.
7. Peng, H., et al. (1991) "HPV types 16 and 33, herpes simplex virus type 2 and other risk factors for cervical cancer in Sichuan province, China" *Int. J. Cancer* 47:711–6.
8. Munoz, N., et al. (1992) "The causal link between HPV and invasive cervical cancer: A population-based case-control study in Columbia and Spain" 52:743–9.
9. Bauer, H. M., et al. (1991) "Genital HPV infection in female university students as determined by a PCR-based method" *JAMA* 265:472–7.
10. Lungu, O., et al. (1992) "Typing of HPVes by polymerase chain reaction amplification with the L1 consensus primers and RFLP analysis" *Mol. Cell Probes* 6:145–52.
11. Scheffner, M., et al. (1990) "The E6 oncoprotein encoded by HPV types 16 and 18 promotes the degradation of p53" *Cell* 63:1129–36.
12. Werness, B., et al. (1990) "Association of HPV types 16 and 18 proteins with p53" *Science* 248:76–9.
13. Lungu, O., et al. (1992) "Relationship of HPV type to grade of cervical intraepithelial neoplasia" *JAMA* 267:2493–6.
14. Lungu, O., et al. (1991) "Biologic properties and nucleotide sequence analysis of HPV type 51" *J. Virol.* 65:4216–25.
15. Lorincz, A. T., et al. (1992) "HPV infection of cervix: Relative risk association of 15 common anogenital types" *Obstet. Gynecol.* 79:328–37.
16. Kirnbauer, R., et al. (1994) "A Virus-Like Particle Enzyme-Linked Immunosorbent Assay Detects Serum Antibodies in a Majority of Women Infected with HPV Type 16" *J. Natl. Cancer Inst.* 86:494–499.
17. Onda, T., et al. (1993) "Association of the Antibodies Against HPV 16 E4 and E7 proteins with cervical cancer positive for HPV DNA" *Int. J. Cancer* 54:624–628.
18. Beaucage and Carruthers (1981) *Tetrahedron Lett.* 22:1859–1862.
19. Needham-VanDevanter, D. R., et al., (1984) *Nucleic Acids Res.* 12:6159–6168.
20. Pearson, J. D. and Regnier, F. E. (1983) *J. Chrom.* 255:137–14976.
21. Maxam, A. M. and Gilbert, W. (1980) *Methods in Enzymology* Grossman, L. and Moldave, D., eds. Academic Press, New York, 65:499–560.
22. Innis, M., et al., eds. (1990) *PCR Protocols: A Guide to Methods and Applications* Academic Press, San Diego.

What is claimed is:

1. A method of detecting only high oncogenic-risk types of human papillomavirus in a subject which comprises:
   a) obtaining from a subject a specimen containing cervical cells;
   b) treating the specimen so as to separately recover nucleic acid molecules present in the cervical cells;
   c) contacting the resulting nucleic acid molecules with multiple pairs of single-stranded labeled oligonucleotide primers selected from the group consisting of SEQ ID Nos 5 and 6, 7 and 8, 11 and 12, 15 and 16, 19 and 20, 21 and 22, 25 and 26, 33 and 34, 35 and 36, and 37 and 38, each such pair being capable of specifically hybridizing with a different high oncogenic-risk type of human papillomavirus but not with a low oncogenic-risk type of human papillomavirus, under hybridizing conditions;
   d) amplifying any nucleic acid molecules to which a pair of primers hybridizes so as to obtain a double-stranded amplification product;
   e) treating any such double-stranded amplification product so as to obtain single-stranded nucleic acid molecules therefrom;
   f) contacting any resulting single-stranded nucleic acid molecules with multiple single-stranded labeled oligonucleotide probes selected from the group consisting of SEQ ID Nos 41, 42, 44, 45, 48, 49, 51, 55, 56, and 57, each such probe containing the same label and being capable of specifically hybridizing with such high oncogenic-risk types of human papillomavirus but not with the low oncogenic-risk type of human papillomavirus, under hybridizing conditions;
   g) contacting any resulting hybrids with a detectably labeled antibody which is capable of specifically forming a complex with the labeled probe, when the probe is present in such a complex, under complexing conditions; and
   h) detecting the presence of any resulting complexes, the presence thereof being indicative of only high oncogenic-risk types of human papillomavirus in the initial specimen.

2. The method of claim 1, wherein the nucleic acid molecule is DNA, RNA or cDNA.

3. The method of claim 1, further comprising analyzing any amplification product of step (d) to determine the identity of the type of human papillomavirus present in the original specimen.

4. The method of claim 1, wherein the high oncogenic-risk type human papillomavirus is selected from a group consisting of: human papillomavirus 16, human papillomavirus 18, human papillomavirus 31, human papillomavirus 33, human papillomavirus 35, human papillomavirus 39, human papillomavirus 45, human papillomavirus 56, human papillomavirus 58, and human papillomavirus 65.

5. The method of claim 1, further comprising performing a Papanicolaou test on the specimen.

6. The method of claim 1, wherein each primer pair and probe is capable of hybridizing with a unique nucleic acid sequence within the E6 open reading frame of each different type of human papillomavirus.

7. The method of claim 1, wherein the single-stranded oligonucleotide primers are labeled with biotin.

8. The method of claim 1, wherein the single-stranded oligonucleotide probes are labeled with fluorescein.

9. The method of claim 1, wherein the antibody is labeled with alkaline-phosphatase.

* * * * *

UNITED STATES PATENT AND TRADEMARK OFFICE
CERTIFICATE OF CORRECTION

PATENT NO. : 5,888,724      Page 1 of 1
DATED : March 30, 1999
INVENTOR(S) : Saul J. Silverstein, et al.

It is certified that error appears in the above-identified patent and that said Letters Patent is hereby corrected as shown below:

<u>Claims,</u>

<u>Column 39, claim 1,</u>
Line 59, "45" should read -- 46 --

Signed and Sealed this

Ninth Day of October, 2001

*Attest:*

*Nicholas P. Godici*

*Attesting Officer*

NICHOLAS P. GODICI
*Acting Director of the United States Patent and Trademark Office*